US006579847B1

(12) United States Patent
Unger

(10) Patent No.: US 6,579,847 B1
(45) Date of Patent: Jun. 17, 2003

(54) METHOD AND APPARATUS FOR VASCULAR NEUROMUSCULAR BLOCKADE

(75) Inventor: Evan C. Unger, Tucson, AZ (US)

(73) Assignee: Imarx Therapeutics Inc., Tucson, AZ (US)

( * ) Notice: Subject to any disclaimer, the term of this patent is extended or adjusted under 35 U.S.C. 154(b) by 0 days.

(21) Appl. No.: 09/563,765

(22) Filed: May 1, 2000

(51) Int. Cl.⁷ .................... A61K 38/00; B05D 3/04; A61F 2/02; A61F 2/06; A61M 5/32
(52) U.S. Cl. ................ 514/2; 427/2.24; 427/2.38; 427/338; 623/1; 623/11; 604/265
(58) Field of Search ............... 514/2, 21; 427/2.24, 427/2.28, 338; 623/1, 11; 604/265

(56) References Cited

U.S. PATENT DOCUMENTS

| 5,356,433 A | | 10/1994 | Rowland et al. ............... 623/11 |
| 5,380,299 A | * | 1/1995 | Fearnot et al. ............... 604/265 |
| 5,660,873 A | * | 8/1997 | Nikolyaychik et al. .... 427/2.24 |
| 5,756,468 A | | 5/1998 | Johnson et al. ................ 514/21 |
| 5,766,605 A | * | 6/1998 | Sanders et al. ............. 424/239 |
| 5,980,972 A | | 11/1999 | Ding ........................ 427/2.24 |

* cited by examiner

Primary Examiner—Christopher S. F. Low
Assistant Examiner—Abdel A. Mohamed
(74) Attorney, Agent, or Firm—Parsons & Goltry; Robert A. Parsons; Michael W. Goltry

(57) ABSTRACT

Method and apparatus of vascular neuromuscular blockade including percutaneous delivery of a quantity of neurotransmitter inhibiting agent to an affected region of a vessel.

6 Claims, 2 Drawing Sheets

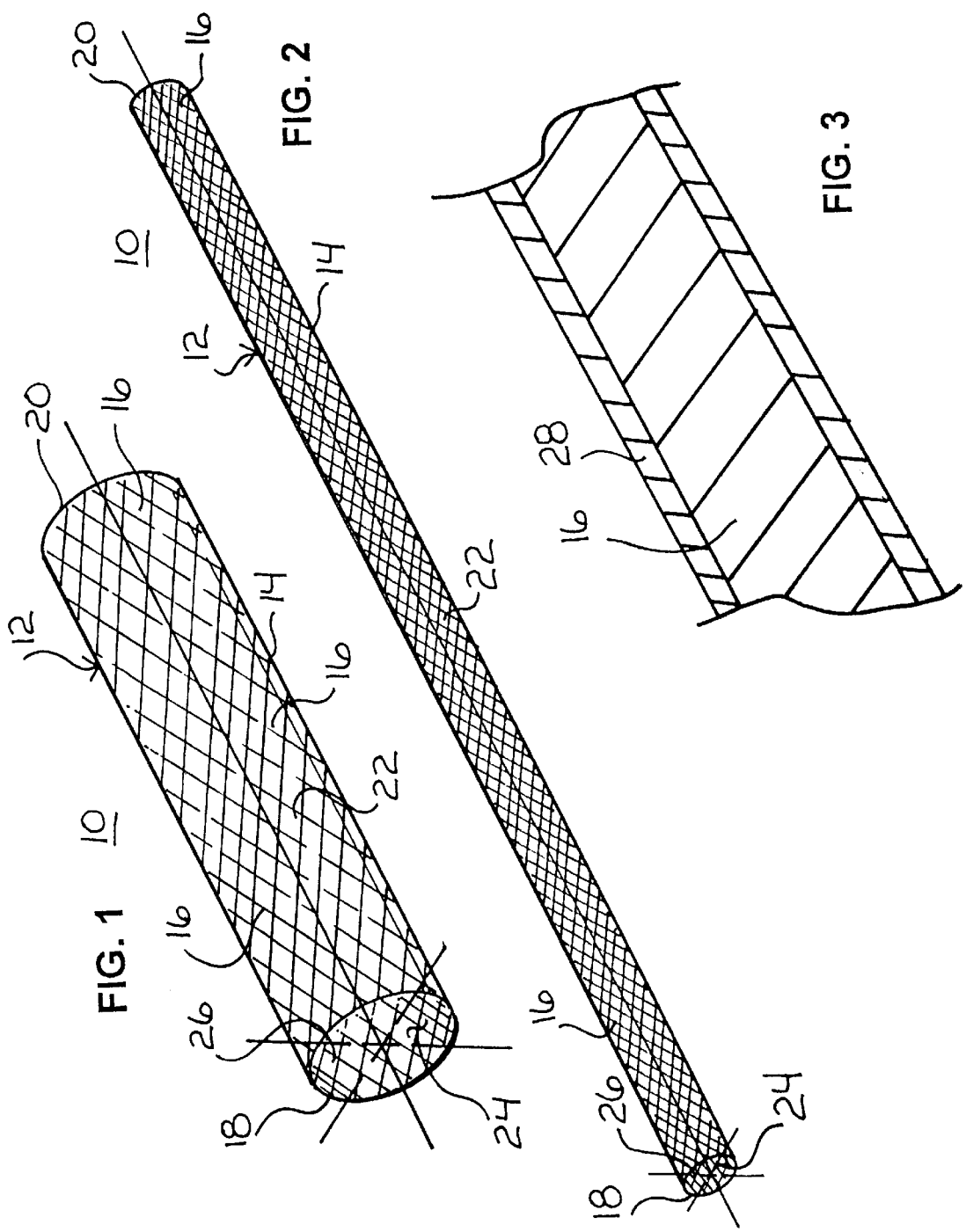

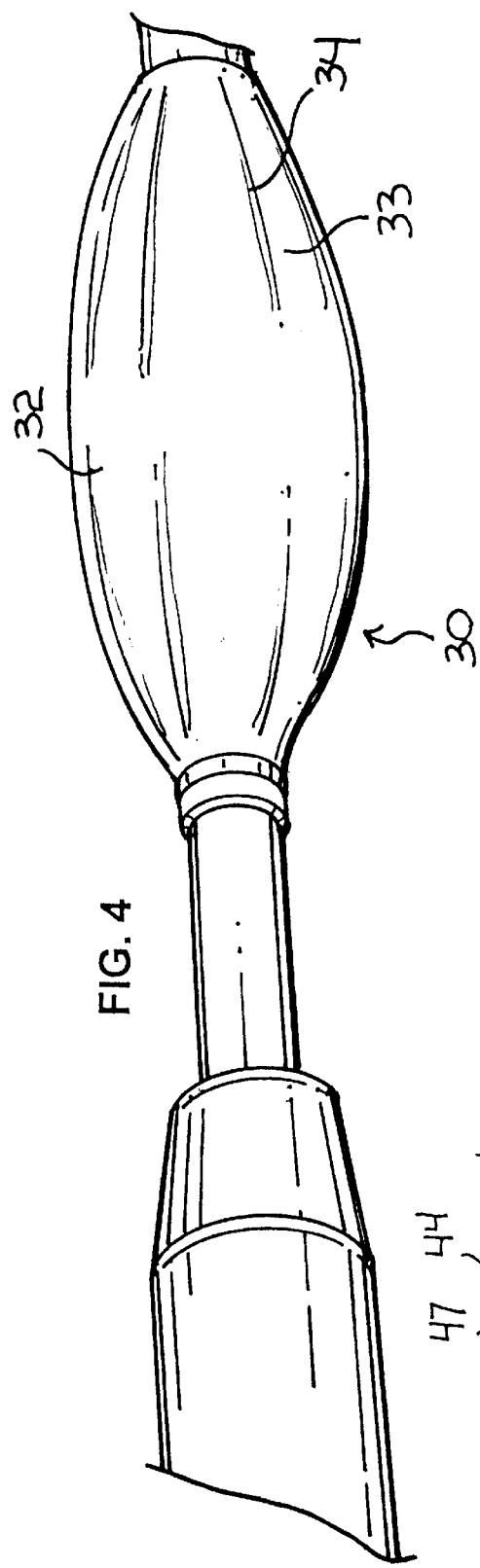
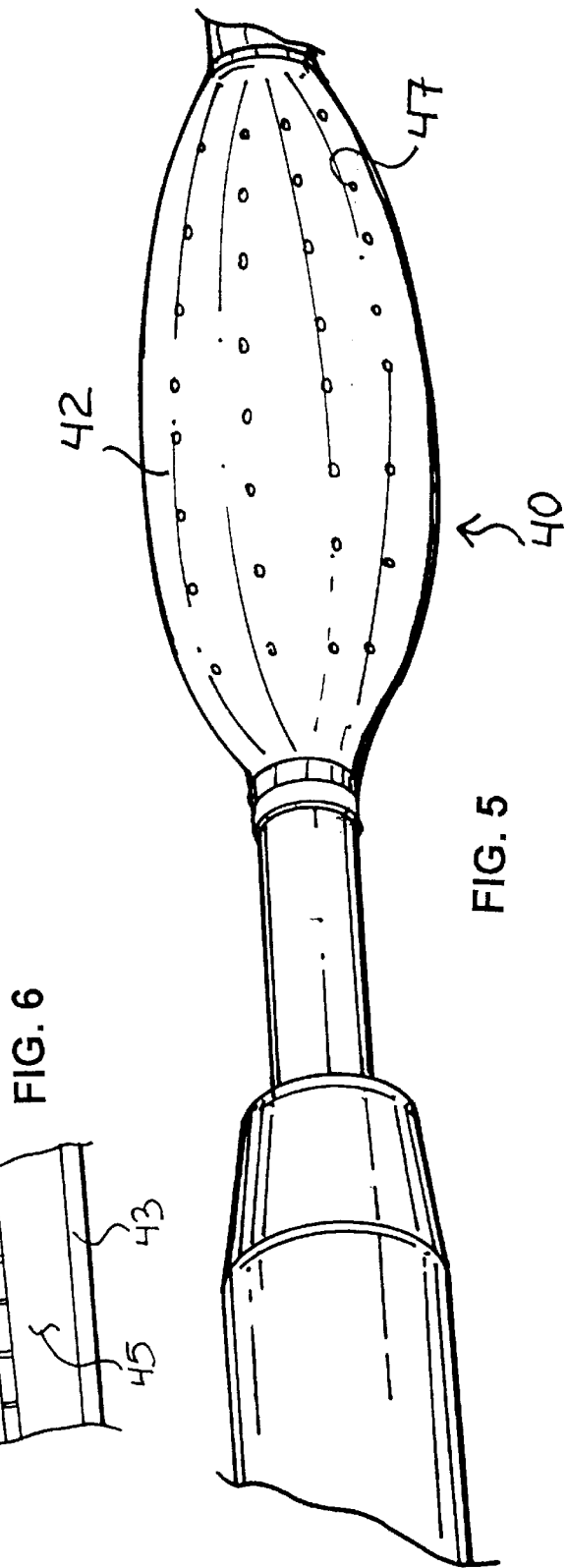
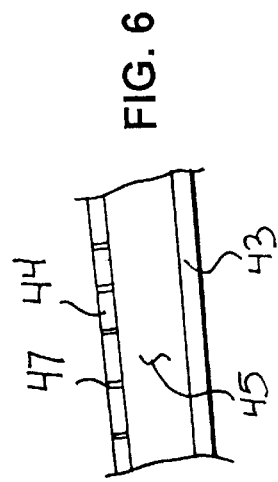
FIG. 4
FIG. 5
FIG. 6

METHOD AND APPARATUS FOR VASCULAR NEUROMUSCULAR BLOCKADE

BACKGROUND OF THE INVENTION

1. Field of the Invention

This invention relates to medical methods and apparatus.

More particularly, this invention relates to methods and apparatus for vascular neuromuscular blockade.

In a further and more specific aspect, the instant invention relates to methods and apparatus for improving vascular patency.

2. Prior Art

The human cardiovascular system is a closed tubular system in which blood, propelled by a muscular heart, flows through vessels to and from all parts of the body. Two circuits, the pulmonary and the systemic, consist of arterial, capillary, and venous components.

These vessels are unfortunately prone to a variety of maladies, which can inhibit the flow of blood, ultimately causing substantial and serious bodily injury. For instance, the coronary arteries, which originate in the aorta and supply blood to the muscular tissue of the heart, are susceptible to atherosclerosis. Atherosclerosis is characterized by the narrowing of the artery from the deposition of atheromatous plaques containing cholesterol and lipids.

The prior art has provided certain procedures for correcting atherosclerosis. If an artery is incompletely obstructed, medication can be used for clearing the obstruction. Another commonly used technique is to surgically bypass the diseased portion if medication is not effective. This method is invasive, requires substantial recovery time and can be very expensive.

As a result, catheter guided vascular procedures have become more and more common for the treatment of atherosclerotic disease. Angioplasty is commonly employed for dilation of a partly obstructed vessel to restore blood flow. In angioplasty, the vessel is dilated by flattening the atheromatous material against and into the arterial wall. Although there are operative risks, such as emboli and tearing, the results seem to be acceptable and the technique may be repeated, if necessary. The inherent limitation of this corrective technique is that it is not a permanent corrective measure. Thus, in order for it to be effective, it must be periodically repeated, which is undesirable and can lead to considerable expense.

As a result of the inherent deficiencies described above in combination with angioplasty, which is normally used for repairing occlusive maladies or vascular constrictive maladies, a vascular insert that is introduced into the affected vessel proximate an affected area has been developed. The insert, commonly referred to as a stent, is typically a mesh of shape retaining material. The stent is introduced into a vessel for distending and buttressing the vessel outwardly thereby restoring the proper flow of blood through the vessel. The stent is normally permanently introduced into the affected vessel.

Stents are typically formed of a wire mesh, and therefore may only be used for repairing obstructive vesicular maladies, and are not useful for repairing fistula or aneurysms. A different vascular insert, commonly referred to as a graft, is employed to repair fistula or aneurysms. A graft is typically formed of dacron, Gortex and polytetrafluoroethylene materials and is inserted into a damaged vessel for use as a vascular conduit.

Catheter guided vascular procedures have become more and more common for the treatment of atherosclerotic disease. Catheter guided procedures for treating atherosclerosis include angioplasty and stenting. Percutaneous procedures are less invasive than conventional surgery and continue to increase in popularity for restoring blood flow and treating aneurysms. Unfortunately, restenosis or occlusion of a vessel is common after these procedures whether a stent is present or not. Also, smooth muscular contraction within the vessel carrying a graft can collapse the graft.

It would be highly advantageous, therefore, to remedy the foregoing and other deficiencies inherent in the prior art.

Accordingly, it is an object of the present invention to provide methods and apparatus for vascular neuromuscular blockage.

Another object of the present invention is to provide methods and apparatus to reduce restenosis of blood vessels.

And another object of the present invention is to provide methods and apparatus to prevent collapse of grafts in blood vessels.

Yet a further object of the present invention is to provide method and apparatus to eliminate vasospasm which occurs in the cerebral arteries following subarachnoid hemorrhage and in other blood vessels following other insults.

SUMMARY OF THE INVENTION

Briefly, to achieve the desired objects of the instant invention in accordance with a preferred embodiment thereof, provided is a method of vascular neuromuscular blockade including percutaneous delivery of a quantity of neurotransmitter inhibiting agent to an affected region of a vessel. The delivery of the agent is achieved by providing an endovascular device carrying the neurotransmitter inhibiting agent.

The endovascular device is shaped and sized for percutaneous insertion into a blood vessel and includes a collapsed configuration and an expanded configuration. A neurotransmitter inhibiting agent is carried by the device. Insertion and positioning of the device is accomplished with the device in the collapsed configuration. In the expanded configuration, the neurotransmitter inhibiting agent is driven into the walls of the blood vessel.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which:

FIG. 1 is a perspective view of a stent according to the present invention, shown in a normal expanded configuration;

FIG. 2 is a perspective view of the stent shown in FIG. 1, the stent being illustrated as it would appear in a collapsed configuration;

FIG. 3 is an enlarged sectional view of a filament of the stent of FIGS. 1 and 2;

FIG. 4 is a perspective view of an angioplasty balloon according to the present invention;

FIG. 5 is a perspective view illustrating a vascular microvascular injection device according to the present invention; and FIG. 6 is a partial sectional view illustrating the double wall of the microvascular injection device of FIG. 5.

DETAILED DESCRIPTION OF THE PREFERRED EMBODIMENT

The present invention eliminates or reduces restenosis or occlusion of blood vessels by percutaneous delivery of a quantity of neurotransmitter inhibiting agent to an affected region of a vessel. It has been found that introduction of a neurotransmitter inhibiting agent to the vessel walls markedly improves vascular patency.

The neurotransmitter inhibiting agent is a pharmacological agent which causes neuromuscular blockade by decreasing transmission of acetylcholine. This agent is used in this invention in concert with a local delivery system for delivery of the agent to the wall of a blood vessel. The preferred agent is Botulinum toxin. However, other agents, which inhibit release or synthesis of a neurotransmitter may also be used. Such agents include hemicholinium, a synthetic compound which blocks the transport system by which choline accumulates in the terminals of the cholinergic fibers.

Turning now to the drawings, in which like reference characters indicate corresponding elements throughout the several views, attention is first directed to FIG. 1 which illustrates a stent, generally designated 10, shaped and sized for insertion into a blood vessel for repairing specific vascular aberrations. Stent 10 is generally comprised of a framework 12. Framework 12 includes a mesh 14 including a plurality of filaments 16 coupled together in meshing engagement. Filaments 16 are preferably constructed of shape retaining stainless steel, or other materials suitable for introduction into the human body such as nitinol, titanium, tantalum, etc. Framework 12 further includes a first open end 18, a second open end 20, an exterior portion 22, and a lumen 24 defined by interior portion 26. Stent 10 is movable between a normal expanded configuration, as can be seen in FIG. 1, and a collapsed configuration, as can be seen in FIG. 2.

Filaments 16 of stent 10 are coated with a coating 28 of the neurotransmitter inhibiting agent as is more clearly illustrated in FIG. 3. Stent 10 is positioning in the vessel in the collapsed configuration utilizing well known percutaneous surgical procedures. When moved to the expanded configuration, either by self expansion or aided by an angioplasty balloon, filaments 16 press coating 28 against the walls of the vessel, forcing the neurotransmitter inhibiting agent into the muscular media of the vessel. It will be understood by those skilled in the art that stents not having shape memory may also be employed. These stents are placed in position, then expanded by an angioplasty balloon. Furthermore, it is contemplated that a resorbable stent can be employed, with the neurotransmitter inhibiting agent incorporated into the biodegradable matrix of the stent. For example, a scaffolding of a biodegradable material such as those commonly used in suture material, like polylactide, polyglycolide, and copolymers thereof may be used. A neurotransmitter inhibiting agent is incorporated into the matrix of the polymeric material or adsorbed to the surface thereof. An angioplasty balloon is inflated to deploy the biodegradable stent and deliver the agent to the vessel.

Referring now to FIG. 4, an angioplasty balloon generally designated 30 is illustrated. Angioplasty balloons are well known in the art, and therefore will not be described in detail. Angioplasty balloon 30 includes an expandable wall 32 having an outer surface 33. Outer surface 33 is coated with a coating 34 of a neurotransmitter inhibiting agent. Angioplasty balloon 30 is movable between a collapsed configuration and an expanded configuration. Angioplasty balloon 30 is positioning in the vessel in the collapsed configuration utilizing well known percutaneous surgical procedures. When moved to the expanded configuration by inflation with a pressurized gas, wall 32 presses coating 34 against the walls of the vessel, forcing the neurotransmitter inhibiting agent into the muscular media of the vessel.

While other neurotransmitter inhibiting agents can be employed in the same manner, botulinum toxin is the preferred agent. Botulinum toxin is delivered locally to vessel walls by coating endovascular devices such as stents, angioplasty balloons, grafts and microvascular injection delivery devices. Botulinum toxin entering the muscular media of the vessel wall causes a long-lasting neuromuscular blockade. Botulinum toxin type A is obtained from Allergan. The botulinum toxin is provided in a sterile lyophilized form produced from the Hall strain of Clostridium botulinum grown in a medium containing N-Z amine and yeast extract. Botulinum toxin type A blocks neuromuscular conduction by binding to receptor sites on motor nerve terminals, entering the nerve terminals, and inhibiting the release of acetylcholine. Between 1 and 1000 U of botulinum toxin is delivered to the muscular media layer of a blood vessel. It has been found that a quantity in the range of 1 to 100 U is most effective, with an amount in the range of 5 to 25 U preferred.

Various methods of coating stents are known in the art. Typically a coating of material is applied by which the botulinum toxin is carried. Metal stents may be plated with gold. Thiol materials are then bound to the gold-plated surface of the stent. Stents may also be coated with one of a number of polymeric materials such as polytetrafluoroethylene. Similar techniques can be used on other endovascular devices of the present invention. While the coating of botulinum toxin may be formed by covalently bonding the botulinum toxin to the surface of the stent or angioplasty balloon, it is more preferable that the botulinum toxin be immobilized within a matrix and the botulinum toxin itself not be covalently bound to the surface of the endovascular device. In a preferred embodiment, the botulinum toxin is bound within a hydrogel matrix. Useful materials for constructing hydrogels or otherwise immobilizing botulinum toxin on the endovascular device include polyethyleneglycol, polyvinylalcohol, methacrylamide, polypropyleneglycol, hydroxyethylmethacrylate, polyacrylate, caprolactones, anhydrides, polylactides, glycolides, phosphazines, ethylene, vinyl fluoride, ethylene vinyl acetate and copolymers of these various polymers and monomers as well as other polymeric materials as are known in the art as being useful for constructing hydrogels.

In a specific example, an iron stent is coated with gold plating by standard anodizing methods according to the principles of the Nernst Equation (electromotive force potentials, See Danies, F. and Alberty, R. A. Physical Chemistry, $3^{rd}$ Edition. Wiley & Sons, Inc., New York, pp. 241–263). The gold-plated stent is now reacted with a bifunctional hydrocarbon comprised of a thiolate (—SH) on one end and a carboxylic acid on the other end. The thiolate portion reacts with the gold moiety to form the base of a self-assembled monolayer. The carboxylic end is converted to the symmetrical anhydride using trifluoroacetic anhydride. (Yan, L., et al. Langmuir (1997), 13(25), 6704–6712). Botulinum toxin is then added to the activated stents to form a noncovalent coating to the stent surface as detailed below.

To form the botulinum toxin coating on the substrate, while not wishing to be bound by any theory, it is believed that the toxin is best applied in a variation of the method disclosed for fibrin in U.S. Pat. No. 5,660,873 which is incorporated by reference herein.

The concentrations of botulinum toxin in the hydrogel solution determines the thickness of the botulinum toxin coating. In the first example for making thick coats, the concentration of the toxin should range from about 0.001 to about 1000 IU/ml, more preferably from about 0.05 to about 500 IU/ml, and most preferably from about 0.1 to about 100 IU/ml. The concentration of botulinum is preferably no more than about 15 ng/ml. In the second example for thin coats, the concentration of the botulinum should range from about 5 to about 75 mg/ml, more preferably from bout 5 to about 50 mg/ml, and most preferably from about 10 to about 30 mg/ml. The second solution preferably has a concentration that is no more than about 0.0001 IU/ml.

The solution can contain a stabilizing salt to solubilize the botulinum in the solution. The stabilizing salt can be any salt, including sodium chloride, magnesium sulfate, sodium sulfate, potassium chloride, calcium chloride, and mixtures thereof. Preferably, the salt concentration in the solution ranges from about 50 to about 300 moles/liter.

The solution can contain other additives to impact the properties of the botulinum toxin coating and the reaction of the body to the coating after implantation. The additive can be contacted with the solution either as is or as a part of a time-release microcapsule. The time-release microcapsule is typically used where the additive is a medication that is to be released gradually into the body over time.

These additives can include an anti-inflammatory drug to suppress inflammation of tissue after implantation of the endovascular device. Anti-inflammatory drugs preferably include antihistamines, glucocorticoids, non-steroidals, salicylates, steroids, and derivatives and mixtures thereof. The anti-inflammatory drug is generally used in the solution at pharmacological concentrations.

Another additive is an inhibitor of smooth muscle cell growth. In intravascular applications, smooth muscle cells in the blood vessel wall can grow into the blood vessel. The constriction of the luminal area of the blood vessel can cause partial or complete blockage of the blood vessel. Inhibitors of smooth muscle cell growth retard the formation of such constrictions. Preferred inhibitors include nitric oxide donors such as nitrosoglutathione, substrates for nitric oxide production such as L-arginine, and derivatives and mixtures thereof. The inhibitor is generally injected concurrently with stent application or may be applied as part of the stent coating solution of pharmacological concentrations. Specifically, the concentration of L-arginine ranges from about 0.1 to about 5.0 .mu.M and nitrosoglutathione from about 0.1 to about 50 .mu.M.

Yet another additive is an antineoplastic reagent. Antineoplastic reagents are particularly useful for substrates contacting a cancerous cell growth to inhibit cell proliferation in the growth. Preferred antineoplastic reagents include doxorubicin, paclitaxel, methotrexate, and derivatives and mixtures thereof. The antineoplastic reagent is generally used at pharmacological concentrations. Specifically, doxorubicin preferably has a concentration in the second liquid ranging from about 0.1 to about 1.0 mg/ml.

And another additive is an antibiotic. Antibiotics are used to prevent infection after implantation of the substrate. Preferred antibiotics include all broad and medium spectrum agents, including aminoglycolides, cephalosporons ($1^{st}$, $2^{nd}$, and $3^{rd}$ generation), macrolides, penicillins, tetracyclines, and derivatives and mixtures thereof. The antibiotic is generally used at pharmacological concentrations. Specifically, tobramycin preferably has a concentration in the second liquid ranging from about 10 to about 50 mg/ml.

Thrombolytic agents may also be incorporated along with botulinum toxin into the coating materials on the stent, balloon or other endovascular device. Useful thrombolytic agents include but are not limited to tissue plasminogen activator, urokinase, heparin, heparan sulfate, warfarin, streptokinase and hirudin. The coating may also include other agents to inhibit thrombosis like antibodies such as abciximab and peptides such as RGD analogues to the activated GPIIBIIIA receptor of activated platelets.

Endovascular devices can be coated with botulinum toxin by immersing a properly prepared device such as a stent within a solution of botulinum toxin. During immersion of the stent in the toxin solution the temperature of the liquid is preferably maintained below the temperature at which denaturing of the botulinum occurs. In botulinum, denaturing typically occurs at temperatures of 56 degrees C. or more. The botulinum toxin may be mixed with another material such as human serum albumin to aid in stabilizing the botulinum toxin protein from denaturation during the coating process. In this case, botulinum toxin may range from about 0.1% by weight to about 90% by weight compared to the other materials used in the coating process.

It is preferred that the temperature of the endovascular device be maintained as closely as possible at the temperature of the body in which the substrate is to be implanted (e.g., 37 .degree.C. for humans) in the body. Such a temperature favors the formation of a botulinum toxin coating having properties that closely resemble those of native botulinum toxin.

The time of immersion of the substrate in the solution also is a factor in determining the thickness of the botulinum toxin coating. Preferably, the thickness of the botulinum toxin coating after immersion ranges from about 400 to about 5,000 microns. To obtain this thickness, the time of immersion preferably ranges from about 4 to about 20 hrs.

The humidity of the ambient atmosphere is another important factor to botulinum toxin coat formation. Preferably, the humidity of the atmosphere is no less than about 90%, more preferably no less than about 92%, and most preferably no less than about 96%.

As will be appreciated, a combination of immersion and spraying of the toxin solution can also apply the botulinum toxin. Immersion of the endovascular device in the solution is preferred because this creates greater surface contact area, greater coating flexibility, and a more uniform coating.

As another alternative, the botulinum toxin can be applied to the substrate as a solid rather than as a liquid. However for purposes of simplicity and cost, it is preferred to apply botulinum toxin to the endovascular device as a liquid.

After formation of the botulinum toxin coating, the coating can be dried at a temperature and pressure and for a time sufficient to vaporize a substantial portion of the water in the botulinum toxin coating and thereby cause the coating to adhere strongly to the endovascular device. After formation, the botulinum toxin coating has a water content ranging from about 80 to about 96% by weight. As noted above, it is believed that removal of water from the botulinum toxin coating has several advantages, including the ability to store the botulinum toxin coating for extended periods before use and increased adhesion of the coating to the substrate surface. While not wishing to be bound by any theory, it is believed that water acts as a lubricant between the botulinum toxin coating and the endovascular device and that the water increases the thickness of the coating and decreases the ability of the botulinum toxin molecules to contact one another. In each case, the net result is a decrease in the adhesive forces between the coating and the endovascular device and the shear strength of the coating. Removal of the water increases the adhesive forces and the shear strength of the coating.

The temperature of the coating during drying is below the melting point of the substrate. Preferably, the coating temperature ranges from about 37 degrees to about 65 degrees C., more preferably from about 45 degrees to about 52 degrees C., and most preferably from about 50 degrees C. to about 51 degrees C.

The pressure during drying is preferably maintained at about atmospheric pressure. The use of higher or lower pressures can significantly increase the cost of the drying equipment.

The time of drying is selected to remove a substantial portion of the water from the coating while suppressing denaturing of the botulinum toxin for drying temperatures in excess of the temperature at which denaturing occurs. Preferably, the time is selected such that drying reduces the water content of the coating to no more than about 8% by weight, more preferably no more than about 5% by weight, and most preferably no more than about 3% by weight. Preferably, the time is also selected such that no more than about 19% by weight, more preferably no more than about 15% by weight, and most preferably no more than about 13% by weight of the botulinum toxin in the botulinum toxin coating is denatured after drying. Accordingly, the time ranges from about 2 to about 24 hrs, more preferably from about 4 to about 20 hrs, and more preferably from about 6 to about 18 hrs.

The composition of the ambient atmosphere during drying is an important aspect of the drying step. The atmosphere should be sterile and have less than a saturation amount of water vapor to facilitate water removal from the coating. Preferably, the atmosphere is substantially composed of an inert gas, such as nitrogen or argon.

After drying, the thickness of the botulinum toxin coating is reduced and the density of the coating increased. Typically, the thickness of the botulinum toxin coating after drying is no more than about 5% of the thickness of the coating before drying. As a consequence, the thickness of the coating after drying preferably ranges from about 10 to about 200 microns.

Before implantation of the dried botulinum toxin coating in a body, it is important to add water, salt, and pharmacological agents to the botulinum toxin coating. Before use, the dried botulinum toxin coating is preferably contacted with water and salts to increase the flexibility of the coating to acceptable levels for implantation. The moisture content of the dried botulinum toxin coating is preferably increased by immersing the coating in water or exposing the coating to water vapor. Surprisingly, the thickness of the coating after rehydration is less than the coating thickness before drying. Relative to stents, the reduced thickness provides an increased luminal area of a stent. The stent is then washed with water and is available for insertion and stent placement.

Botulinum toxin may also be incorporated into grafts, e.g. dacron, Gortex and polytetrafluoroethylene materials for implantation into the body for use as vascular conduits. Botulinum toxin then is released locally and inhibits smooth muscle contraction and helps to prevent the graft from collapsing. The polytetrafluoroethylene graft may further comprise tubular graft members formed of expanded polytetrafluoroethylene having a number of nodes and fibrils with interconnecting nodes and forming a microporous matrix useful for imbibing botulinum toxin. properties.

Angioplasty balloons can be coated with "Super Glue". The "Super Glue" (polymethyacrylate resin) is diluted in toluene and nebulized onto the inflated angioplasty balloon. The angioplasty balloon is then rolled into a container of lyophilized Botulinum toxin such that approximately 5 Units of the toxin is adsorbed onto the surface of the balloon. Methods can be adapted from the general procedure described earlier for stent coating.

Specific examples of endovasculoar devices with botulinum toxin include:

EXAMPLE 1

A balloon dilatation catheter (Boston Scientific, Quincy, MA, model no., 13-188) is coated with PEG and Botulinum toxin as follows: Branched PEG, MW=40,000, Shearwater Polymers, Alabaster is dissolved with botulinum toxin in methyltert-butanol at a PEG concentration=50 mg per ml and a botulinum toxin concentration=10 mg per ml. This material is atomized and deposited on the surfaces of the balloon within a drying chamber. The balloon catheter is dried. The PEG/BT appears as a white powder material coating the surfaces of the balloon. The catheter is then used for an angioplasty. The balloon is inflated at the site of the vessel narrowing. The PEG/BT material impregnates the vessel wall as the balloon is inflated under high pressure. BT causing neuromuscular blockade diminishes smooth muscle proliferation.

EXAMPLE 2

A WALLSTENT (Boston Scientific, Quincy, MA, model no. 42054) metallic stent is coated at described previously. The coated stent is covered by a white PEG/botulinum toxin. The stent is advanced into the iliac artery of a patient with stenotic narrowing due to advanced atherosclerosis. The stent is delivery with the Unistep Plus Delivery System (Boston Scientific). The Stent is positioned and deployed at the site of stenosis. The botulinum toxin aids in prevention of restenosis and the PEG material releases the drug over a delayed period of time for maximal therapeutic benefit.

EXAMPLE 3

Another WALLSTENT (same model) is treated with a gold plating process using electrochemistry to deposit a thin film of gold on the surface of the stent. A different Branched PEG is prepared by substituting the terminal hydroxyl moieties of the PEG with thiol groups. The Branched PEG is mixed in organic solvent (methytertbutanol). The Branched PEG is atomized and sprayed on the stent and dried to a film. The Branched PEG binds covalently to the surface of the stent via thiol groups. The stent is then immersed into an aqueous solution of botulinum toxin at a concentration of 100 U of botulinum toxin per ml. The hydrogel on the surface of the stent imbibes the botulinum toxin and about 10 U of botulinum toxin is adsorbed via the hydrogel onto the surface of the stent. The resulting botulinum toxin laden stent is then ready for use for an endovascular procedure.

EXAMPLE 4

Branched PEG is prepared with substitution of 50% of the ethylene groups with propylene groups and thiolated as described previously and used as a coating material as described previously. The propylene groups prolong the release of the botulinum toxin providing therapy for a longer period of time.

EXAMPLE 5

A patient suffers a subarachnoid hemorrhage and as a complication has vasospasm of the cerebral arteries-particularly involving the left middle cerebral arteries. A Tracker balloon catheter (Boston Scientific) is coated with botulinum toxin and advanced into the left middle cerebral artery. The balloon is inflated driving botulinum toxin into the vessel wall. Vasospasm resolves and blood flow the left cerebral hemisphere is improved.

Turning to FIGS. 5 and 6, to deliver the botulinum toxin to the media of the vessel wall, a microvascular injection device generally designated 40 may be employed as part of an angioplasty procedure, before, after or during a stent placement. Device 40 comprises an balloon catheter 42 movable between a collapsed and expanded configuration. Balloon catheter 42 has an inner wall 43 and an outer wall 44 defining a chamber 45. Outer wall 44 includes a plurality of micropores 47 formed therein. The neurotransmitter inhibiting agent is carried in chamber 45 and expelled through micropores 47 in the expanded configuration. As the balloon is inflated, pressure within chamber 45 drives the agent through micropores 47 into the vessel wall. In this case the botulinum toxin is provided in a liquid form for delivery from the balloon catheter or other microinjection device.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A method of reducing restenosis of a blood vessel comprising:
   providing an endovascular device carrying a quantity of botulinum toxin;
   percutaneously inserting the endovascular device into an affected region of a vessel; and
   applying, by contact from the endovascular device, the botulinum toxin to a muscular media of the vessel.

2. A method as claimed in claim 1 wherein the step of applying the botulinum toxin to a muscular media of the vessel includes diminishing smooth muscle proliferation by neuromuscular blockade.

3. A method as claimed in claim 1 wherein the endovascular device has a collapsed configuration and an expanded configuration, the step of applying the botulinum toxin comprises positioning the endovascular device into the vessel in the collapsed configuration and driving the botulinum toxin into the muscular media of the vessel by expanding the endovascular device to the expanded configuration.

4. A method as claimed in claim 3 wherein the step of providing an endovascular device comprises providing a microvascular injection device comprising a balloon catheter having an inner wall and an outer wall defining a chamber, the outer wall having micropores formed therein, the botulinum toxin carried in the chamber and expelled through the micropores in the expanded configuration.

5. A method as claimed in claim 3 wherein the step of providing an endovascular device comprises applying a coating of the botulinum toxin to the endovascular device.

6. A method as claimed in claim 5 wherein the endovascular device is selected from a group consisting of a stent, a biodegradable stent, an angioplasty balloon, and a graft.

* * * * *